United States Patent [19]

Wee

[11] Patent Number: 4,944,796
[45] Date of Patent: Jul. 31, 1990

[54] CERTAIN 2-(DISUBSTITUTED AMINO) ACETANILIDE HERBICIDES

[75] Inventor: Siok-Hui H. Wee, Berkeley, Calif.

[73] Assignee: ICI Americas Inc., Wilmington, Del.

[21] Appl. No.: 270,573

[22] Filed: Nov. 14, 1988

[51] Int. Cl.$^5$ .................. A01N 37/26; C07C 103/64; C07C 103/82
[52] U.S. Cl. .................. 71/118; 71/100; 71/111; 71/115; 558/238; 558/240; 560/41; 562/449; 564/59; 564/149; 564/155
[58] Field of Search .................. 564/155, 59, 149; 71/118, 100, 111, 115; 558/238, 240; 560/41; 562/449

[56] References Cited

U.S. PATENT DOCUMENTS

| | | | |
|---|---|---|---|
| 3,888,899 | 6/1975 | Greve et al. | 260/465 |
| 3,928,415 | 12/1975 | Greve et al. | 260/470 |
| 4,532,251 | 7/1985 | Spatz | 514/354 |
| 4,596,813 | 6/1986 | Spatz | 514/355 |
| 4,623,383 | 11/1986 | Grega née Toth | 71/100 |
| 4,639,468 | 1/1987 | Roncucci et al. | 514/620 |

OTHER PUBLICATIONS

Malatesta et al., Chemical Abstracts, vol. 98 (1983), 125504x.

Primary Examiner—Richard L. Raymond
Attorney, Agent, or Firm—Denis A. Polyn

[57] ABSTRACT

2-(Disubstituted amino)acetamides of the formula

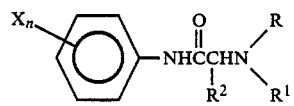

wherein R is alkyl or phenyl; $R^1$ is selected from the group consisting of amino, alkyl, allyl, substituted carbonyl wherein said substituent is haloalkyl, alkoxycarbonyl, alkylthio, carboxy, alkoxy, alkyl, vinyl, haloanilino, phenylthio, alkylamino, benzylamino, alkoxycarbonylalkyl or substituted carbamyl wherein the substituent is alkyl halocarbanilide; alkylthio thiocarbonyl; or mono-haloanilino carbonylmethylene, alkoxy carbonylmethylene, or carboxymethylene; $R^2$ is hydrogen, alkyl or phenyl; X is halo or haloalkyl; and n is an integer selected from 1-3, inclusive; the compounds are useful as herbicidal agents.

26 Claims, No Drawings

CERTAIN 2-(DISUBSTITUTED AMINO) ACETANILIDE HERBICIDES

This invention relates to certain 2-(disubstituted amino) acetanilide herbicides, to their use in herbicidal formulations and a process for the preparation of the compounds. In particular, this invention relates to the compounds corresponding to the formula

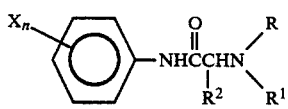

wherein
R is alkyl or phenyl;
$R^1$ is selected from the group consisting of amino, $C_1$–$C_6$ alkyl, allyl, or substituted carbonyl wherein said substituent is haloalkyl, alkoxycarbonyl, alkylthio, carboxy, alkoxy, alkyl, vinyl, haloanilino, phenylthio, alkylamino, benzylamino, alkoxycarbonylalkyl or substituted carbamyl wherein the substituent is alkyl halocarbanilide; alkylthio thiocarbonyl; or monohaloanilino carbonylmethylene, alkoxycarbonylmethylene or carboxymethylene;
$R^2$ is hydrogen, $C_1$–$C_6$ alkyl or phenyl;
X is halo, haloalkyl or combinations thereof; and
n is the integer selected from 0–3, inclusive.

The compounds of the present invention, as will be seen from the description and test data which follows, have utility as pre-emergence and post-emergence herbicides against a wide range and variety of plant species.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn and dwarfing. The term "herbicidally effective amount" is used to denote any amount of the compound which achieves such control or modification when applied to the undesired plants themselves or to the proximate area in which these plants are growing, or in the case of pre-emergence application the plants will be growing. The term "plants" is intended to include germinant seeds, emerging seedlings and established vegetation, including both roots and above-ground portions.

Certain other 2-(disubstituted amino) acetanilides have been found to be useful as fungicides, as in U.S. Pat. Nos. 4,532,251 and 4,596,813; other such compounds have been found to be useful as pharmaceuticals, as in U.S. Pat. Nos. 3,888,889 and 3,928,415; while still other such compounds have been found useful as herbicidal antidotes, as in U.S. Pat. No. 4,623,383. These prior references were found to prepare such compounds by refluxing the requisite alpha-haloacetanilide with the primary amine of choice, either in a hydrocarbon solvent or using an excess of the primary amine as the solvent. The present invention provides a novel method for preparing the compounds of this invention.

DETAILED DESCRIPTION OF THE INVENTION AND PREFERRED EMBODIMENTS

Within the scope of the above formula, certain embodiments are preferred, as follows:
R is preferably $C_1$–$C_3$ alkyl or phenyl;
$R^1$ is preferably amino, $C_1$–$C_4$ alkyl, allyl, substituted carbonyl wherein said substituent is $C_1$–$C_4$ haloalkyl, $C_2$–$C_4$ alkoxycarbonyl, $C_1$–$C_4$ alkylthio, carboxy, $C_1$–$C_5$ alkoxy, $C_1$–$C_4$ alkyl, vinyl, haloanilino, phenylthio, $C_1$–$C_4$ alkylamino, benzylamino, $C_3$–$C_6$ alkoxycarbonylalkyl or substituted carbamyl wherein the substituent is $C_1$–$C_2$ alkyl halocarbanilide; $C_2$–$C_4$ alkylthio thiocarbonyl; or monohaloanilino carbonylmethylene, $C_1$–$C_3$ alkoxy carbonylmethylene, or carboxymethylene;
$R^2$ is preferably hydrogen, $C_1$–$C_3$ alkyl or phenyl;
X is preferably halo or $C_1$–$C_2$ haloalkyl; and
n is preferably an integer selected from 1–3, inclusive.

In the compounds where R is alkyl, the more preferred groups are methyl and ethyl; in the compounds where X is halo or haloalkyl, the more preferred groups are mono- and di-fluoro and trifluoromethyl; in the compounds where $R^2$ is alkyl, the more preferred groups are methyl and ethyl. In the compounds where $R^1$ is substituted carbonyl, the more preferred substituent groups are alkylthio, alkoxy, trifluoromethyl and phenylthio.

In the compounds of this invention there are certain preferred and more preferred combinations of substituents when X is fluoro, n is selected from the integers 1 and 2; R is $C_1$–$C_2$ alkyl, $R^1$ is selected from the group amino, carboxymethylene, alkyl, substituted carbonyl wherein said substituent is selected from alkylthio, alkoxy, trifluoromethyl, or phenylthio; and $R^2$ is selected from hydrogen or phenyl. Further, such combinations are more preferred when X is fluoro, n is the integer 2, R is methyl, $R^1$ is selected from the group amino, carboxymethylene, allyl, substituted carbonyl wherein said preferred substituent is selected from methylthio, ethylthio, ethoxy, methoxy, trifluoromethyl and phenylthio, and $R^2$ is hydrogen or phenyl. Still further combinations will be apparent from the compounds listed herein.

The term "alkyl" and related terms, such as alkoxy and alkylthio, are used herein to include both straight and branched chain saturated acyclic hydrocarbyl moieties and includes moieties having the indicated carbon atoms, usually in the range of from one to six carbon atoms, such as methyl, ethyl, n-propyl, isopropyl, n-butyl, isobutyl, secbutyl, n-pentyl, isopentyl, n-hexyl, isohexyl, and the like. The term "halo" includes, unless otherwise provided, fluorine, chlorine, bromine or iodine as mono-, di-, tri-, or per-, and possibly mixed halogen substituents.

As mentioned above, the compounds of this invention have been found to be active herbicides in possessing herbicidal activity against various species of plants. In the broadest sense, the term "weeds" refers to plants which grow in locations in which they are not wanted. This invention therefore also relates to herbicide methods and herbicidal compositions useful for controlling undesirable vegetation, comprising applying to a locus where control of such vegetation is desired an herbicidally effective amount of a compound as described herein, and as to the herbicidal compositions comprising an herbicidally effective compound as described herein together with an inert diluent or carrier and adjuvants suitable for use with herbicide compositions.

The compounds of the present invention may be prepared by a variety of synthesis routes, depending on the substituent groups. Some of these routes are described in the following schemes.

The herbicidally active 2-(disubstituted amino) acetanilides, and the 2-(monosubstituted amino) acetanilide intermediates of the present invention also can be prepared by reacting the alpha-haloacetanilide with the primary amine, or methyl hydrazine of choice in an alcohol solvent, in the presence or absence of water, at substantially ambient temperature as shown by the following Scheme I:

Scheme I

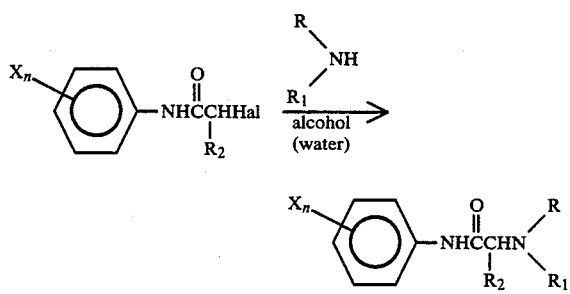

wherein R is alkyl or phenyl; $R^1$ is hydrogen or amino; $R^2$ is hydrogen, $C_1$–$C_6$ lower alkyl or phenyl; X is halo, haloalkyl or combination thereof; and n is an integer selected from 0–3, inclusive.

Where the compounds of Scheme I are the 2-(monosubstituted amino) acetanilide intermediates, wherein $R^1$ is hydrogen, they can be further reacted with an acylating or alkylating agent as shown by the following Schemes II, III and IV:

Scheme II

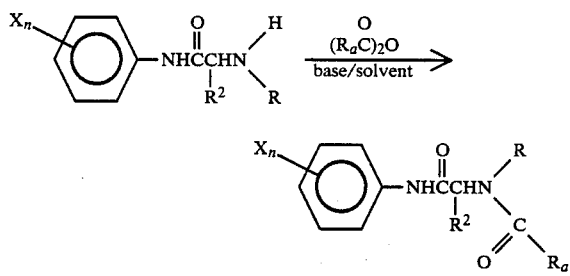

Scheme III

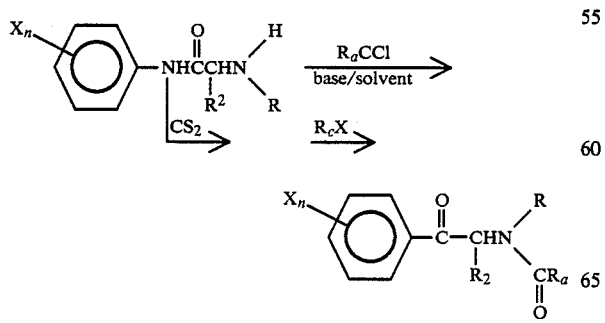

Scheme IV

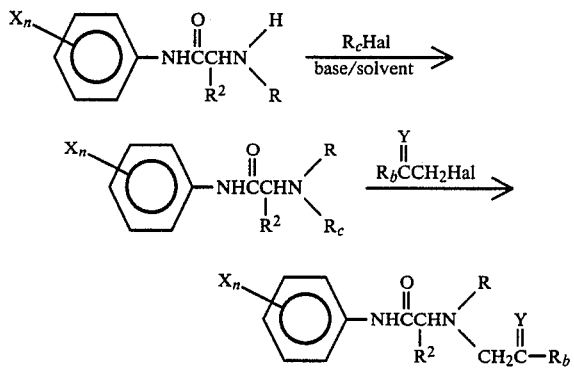

wherein $R_a$ is alkoxy, haloalkoxy, allyl, vinyl, alkoxycarbonyl, hydroxy, carbohydroxy, phenylthio, dialkylamino or carboalkoxy; Y is oxygen or sulfur; and R, $R^2$, X and n are as defined above; $R_b$ is monohaloanilino, alkoxy, alkylthio, mercapto or hydroxy; and $R_c$ is allyl or lower alkyl.

The following are examples of compounds which have been synthesized by the procedures described above. These examples are offered strictly for the purpose of illustration, and are intended neither to limit nor define the invention in any manner. The structures were confirmed by infrared spectroscopy (IR), nuclear magnetic resonance (NMR) or mass spectroscopy (MS).

EXAMPLE 1

Preparation of Intermediate: 2'-Fluoro-2-methylamino acetanilide

To an ethanolic (70 ml) solution of N-(2-fluoro)phenyl-2-chloroacetamide (21.6 g, 0.11 mol) was added 40% aqueous methylamine (70 ml) and stirred at room temperature overnight. The mixture was concentrated on a rotary evaporator. The product was extracted into ethyl ether (200 ml) and the organic layer dried with magnesium sulfate (MgSO4) and concentrated. The crude product was passed through a short column of silica gel using 1:1 methylene chloride-hexane as the eluent. The product obtained was a yellow oil weighing 18.2 g (88% yield).

EXAMPLE 2

Preparation of Intermediate: 3'-Trifluoromethyl-2-methylamino acetanilide

To an ethanolic solution (50 ml) of N-(3-trifluoromethyl)phenyl-2-bromoacetamide (2.8 g, 0.01 mol) cooled in an ice/water bath was added subsurface methylamine until saturation was reached. The mixture was stirred overnight at ambient temperature, then concentrated by rotary evaporator. The product was extracted into dichloromethane, washed with water and the organic layer dried with magnesium sulfate and evaporated to dryness by rotary evaporator to yield 2.2 g (95% yield) of an oil.

EXAMPLE 3

Preparation of N-Methyl-N-trifluoroacetyl-2',5'-difluoro-2-aminoacetanilide

To a methylene chloride solution (20 ml) of 2,5-difluorosarcosine anilide (2.0 g, 10 mmol) and pyridine (0.9 g, 11 mmol) was added trifluoroacetic anhydride (2.3 g, 11 mmol) and stirred for 2 hours at room temperature. The mixture was washed with water (10 ml), dried with MgSO4 and concentrated to give 1.8 g (61%) of the desired product.

EXAMPLE 4

Preparation of N-Ethoxycarbonyl-N-methyl-2',5'-difluoro-2-aminoacetanilide

To a methylene chloride solution (20 ml) of 2',5'-difluoro-2-phenylsarcosine anilide (2.5 g, 9 mmol) and pyridine (0.9 g, 10.8 mmol) cooled in ice bath, was added ethyl chloroformate (1.0 g, 9 mmol) through an addition funnel and stirred at room temperature overnight. The mixture was washed with water, dried with MgSO4 and concentrated. The product was purified by filtering through a short column of silica gel using 25% ethyl acetate in hexane to give 2.4 g (80%) of a thick oil.

EXAMPLE 5

Preparation of N-Ethoxycarbonylmethyl-N-methyl-2',5'-difluoro-2-aminoacetanilide To a dimethylformamide solution (75 ml) of 2,5-difluorosarcosine anilide (5.0 g, 25 mmol) was added potassium carbonate (3.5 g, 25 mmol) and ethyl bromoacetate (4.2 g, 25 mmol). The mixture was heated to 100° C. for 4 hours and the reaction was followed by thin layer chromatography. The solvent was removed under reduced pressure. The residue was dissolved in methylene chloride (75 ml) and washed with water (3×25 ml). The organic layer was dried with magnesium sulfate and filtered through a thin pad of silica gel. The solvent was removed under a rotary evaporator to give a yellow oil (4.6 g, 64%) of the desired product.

These and further compounds prepared by similar procedures are listed in Table I below, together with physical data in the form of refractive indices or melting points where such measurements were possible, and physical description where measurements were not possible.

TABLE OF COMPOUNDS $$X_n\text{-C}_6H_4\text{-NHC(O)CHN(R)(R^1), R^2}$$

| Compound Number | $X_n$ | R | $R^1$ | $R^2$ | Physical Constant |
|---|---|---|---|---|---|
| 1 | 2,5-di-F | —CH$_3$ | —C(O)CF$_3$ | H | 60–70° C. |
| 2 | 2-F | —CH$_3$ | —CH$_3$ | H | thick oil |
| 3 | 2-F | —CH$_3$ | —CH$_2$C(O)NH-(2-F-C$_6$H$_4$) | H | 240–243° C. |
| 4 | 2,5-di-F | —CH$_3$ | —C(O)CH$_2$Cl | H | 137–140° C. |
| 5 | 2,5-di-F | —CH$_3$ | —CH$_2$COCH$_2$CH$_3$ | H | yellow oil |
| 6 | 2-F | —CH$_3$ | —COC$_3$H$_9$-i | H | oil |
| 7 | 2,5-di-F | —CH$_3$ | —C(O)N(CH$_3$)—CH$_2$C(O)—N(2,5-di-F-C$_6$H$_3$) | H | 55–60° C. |
| 8 | 2,5-di-F | —CH$_3$ | —CH$_2$CH=CH$_2$ | H | thick oil |
| 9 | 2-F | —CH$_3$ | —CH$_2$COCH$_2$CH$_3$ | H | oil |
| 10 | 2,5-di-F | —CH$_3$ | —CC(O)OCH$_2$CH$_3$ (—C(O)C(O)OCH$_2$CH$_3$) | H | 95–100° C. |

TABLE OF COMPOUNDS-continued $$X_n-\text{C}_6\text{H}_4-\text{NHCCHN}\begin{matrix}R\\R^1\end{matrix}$$
with $R^2$ on the central carbon, and the central C=O

| Compound Number | $X_n$ | R | $R^1$ | $R^2$ | Physical Constant |
|---|---|---|---|---|---|
| 11 | 2-F | —CH$_3$ | —CCH$_2$Cl (C=O) | phenyl | 135–140° C. |
| 12 | 3-CF$_3$ | —CH$_3$ | —CCH$_2$Cl (C=O) | phenyl | 148–150° C. |
| 13 | 2,5-di-F | —CH$_3$ | —CCH=CH$_2$ (C=O) | H | 98–100° C. |
| 14 | 2,5-di-F | —CH$_3$ | —CCHCH$_2$ (C=O, Br, Br) | H | thick oil |
| 15 | 2,5-di-F | —CH$_3$ | —CCH$_2$Cl (C=O) | phenyl | 148–150° C. |
| 16 | 2-F | —CH$_3$ | —NH$_2$ | phenyl | oil |
| 17 | 2,5-di-F | —CH$_3$ | —CH$_2$COH (C=O) | H | 140–145° C. |
| 18 | 2-F | —CH$_3$ | —CH$_2$COC$_2$H$_5$ (C=O) | phenyl | thick oil |
| 19 | 2,5-di-F | —CH$_3$ | —CH$_3$ | H | 62–64° C. |
| 20 | 3-F | —CH$_3$ | —CH$_2$COH (C=O) | H | 173–175° C. |
| 21 | 2,5-di-F | —CH$_3$ | —NH$_2$ | phenyl | thick oil |
| 22 | 2,5-di-F | —CH$_3$ | —CSCH$_2$CH$_3$ (C=O) | H | 99–101° C. |
| 23 | 2,5-di-F | —CH$_3$ | —CCOCH$_2$CH$_3$ (C=O, C=O) | phenyl | 127–131° C. |
| 24 | 2,5-di-F | —CH$_3$ | —CCOH (C=O, C=O) | phenyl | thick oil |

TABLE OF COMPOUNDS-continued

Structure: $X_n$-phenyl-NHC(O)CH(R)N(R^1)(R^2)

| Compound Number | $X_n$ | R | $R^1$ | $R^2$ | Physical Constant |
|---|---|---|---|---|---|
| 25 | 3-CF$_3$ | —CH$_3$ | —C(O)C(O)OC$_2$H$_5$ | phenyl | 115–120° C. |
| 26 | 2,5-di-F | —CH$_3$ | —C(O)SCH$_2$CH$_3$ | phenyl | thick oil |
| 27 | 2,5-di-F | —CH$_3$ | —C(O)OCH$_2$CH$_3$ | phenyl | thick oil |
| 28 | 2,5-di-F | —CH$_3$ | —C(O)OC$_2$H$_5$ | H | 96–98° C. |
| 29 | 2,5-di-F | —CH$_3$ | —C(O)OCH$_2$CH(CH$_3$)$_2$ | H | 71–73° C. |
| 30 | 2,4-di-F | phenyl | —C(O)CH$_2$CH(CH$_3$)$_2$ | —CH$_2$CH$_3$ | viscous oil |
| 31 | 2,5-di-F | —CH$_3$ | —C(O)—C$_4$H$_9$-i | phenyl | 56–58° C. |
| 32 | 2,5-di-F | —CH$_3$ | —C(O)—SC$_4$H$_9$-t | phenyl | 133–135° C. |
| 33 | 2,5-di-F | —CH$_3$ | —C(O)—SC$_4$H$_9$-t | H | 156–158 |
| 34 | 3-CF$_3$ | —CH$_3$ | NH$_2$ | phenyl | thick oil |
| 35 | 3-CF$_3$ | —CH$_3$ | —C(O)—SC$_2$H$_5$ | phenyl | thick oil |
| 36 | 2,5-di-F | —CH$_3$ | —C(O)SCH$_3$ | phenyl | 103–106° C. |
| 37 | 2,5-di-F | —CH$_3$ | —C(O)—OCH$_3$ | phenyl | 98–101° C. |

TABLE OF COMPOUNDS-continued

Structure: $X_n$-C$_6$H$_4$-NHC(=O)CH(R$^2$)N(R)-R$^1$

| Compound Number | $X_n$ | R | R$^1$ | R$^2$ | Physical Constant |
|---|---|---|---|---|---|
| 38 | 2,5-di-F | —CH$_3$ | —C(=O)CF$_3$ | phenyl | 118–122° C. |
| 39 | 2,5-di-F | —CH$_3$ | —C(=O)NCH$_3$ | phenyl | 138–141° C. |
| 40 | 3-CF$_3$ | —C$_2$H$_5$ | —C(=O)OC$_2$H$_5$ | H | semi-solid |
| 41 | 3-CF$_3$ | —CH$_2$CH$_3$ | —C(=O)OCH$_2$CH$_3$ | H | semi-solid |
| 42 | 2,5-di-F | —CH$_3$ | —C(=O)S-phenyl | phenyl | 138–141° C. |
| 43 | 2,5-di-F | —CH$_3$ | —C(=O)CH$_3$ | phenyl | 144–146° C. |
| 44 | 2,5-di-F | —CH$_3$ | —C(=O)CH$_2$C(=O)OCH$_2$CH$_3$ | phenyl | 126–129° C. |
| 45 | 2,5-di-F | —CH$_3$ | —C(=O)N(CH$_3$)$_2$ | phenyl | 127–133° C. |
| 46 | 2,5-di-F | —CH$_3$ | —C(=S)SCH$_3$ | phenyl | 125–132° C. |
| 47 | 2,5-di-F | —CH$_3$ | —CH$_3$ | phenyl | 60–68° C. |
| 48 | 3-CF$_3$ | —CH$_2$CH$_3$ | —C(=O)NHCH$_2$-phenyl | H | 146–148° C. |
| 49 | 3-CF$_3$ | —CH$_2$CH$_3$ | —C(=O)NH-(2,4-di-F-phenyl) | H | sticky material |

TABLE OF COMPOUNDS-continued

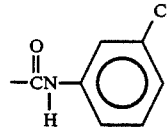

| Compound Number | $X_n$ | R | $R^1$ | $R^2$ | Physical Constant |
|---|---|---|---|---|---|
| 50 | 3-CF$_3$ | —CH$_2$CH$_3$ | (structure with —CN(H)— linked to Cl-phenyl) | H | 150–152° C. |

The compounds listed in the foregoing Table 1 were tested for herbicidal activity by various methods and at various rates of application. Some were tested by more than one method or at more than one rate, but at least one method is shown for each compound to exhibit utility. The following examples are for illustrative purposes only and are not intended as necessariliy representative of the overall testing performed. As one skilled in the art is aware, in herbicidal testing a significant number of factors that are not readily controllable can affect the results of individual tests. For example, the results may vary depending on environmental factors, such as amount of sunlight and water, soil type, pH of the soil, temperature, and humidity, among other factors. Also, the depth of planting and the application rate of the herbicide, as well as the nature of crops being tested, can affect the results of the test. Results may vary from plant species and within the plant varieties. The methods and activity are as follows:

Pre-Emergence Herbicidal Evaluation

Flats were filled with sandy loam soil containing a fungicide and fertilizer. The soil was leveled and rows of grassy weeds, broadleaf weeds and yellow nutsedge (*Cyperus esculentus*), were planted thickly enough so that several seedlings emerged per inch of row. The grassy weeds were: foxtail (*Setaria spp.*), watergrass (*Echinochloa crusgalli*) and wild oat (*Avena fatua*). Broadleaf weeds utilized were annual morningglory (*Ipomoea purpurea*), veletleaf (*Abutilon theophrasti*) and mustard (*Brassica kaber*).

One day after planting, the flats were sprayed with a solution of a test compound at a rate of 80 gallons of solution per acre with the compound being applied at a rate of 4 pounds per acre (4.48 kg/ha).

The solutions of the test compounds were made by weighing out 333 mg of the test compound into a 60 ml wide-mouth bottle, dissolving it in 25 ml of acetone containing 1% Tween ®20 (polyoxyethylene sorbitan monolaurate emulsifier). Additional solvents, not exceeding 5 ml, were used if needed to dissolve the compound. A 20.5 ml aliquot was taken from the stock solution and diluted with 25 ml of an acetone:water mixture (19:1) containing 1% Tween ®20. This was used as the spray solution.

The flats were returned to the greenhouse after spraying and watered daily by sprinkling. The degree of weed control was estimated and recorded 3 weeks after treatment, as percentage control compared to the growth of the same species in an untreated check flat of the same age.

The percent control is based on the total injury to the plants due to all factors, including inhibited germination, killing of the plant tissue after emergence, stunting, malformation, chlorosis, and other types of injury. The control ratings vary from 0 to 100 percent, where 0 represents no effect with growth equal to the untreated control, and 100 represents complete kill.

Post-Emergence Herbicidal Evaluation

The soil was prepared and seeded with the same varieties as described for the pre-emergence test. The flats were placed in the greenhouse at 70°–85° F. and watered by sprinkling. Twelve to fourteen days after planting, the flats were sprayed at a rate of 80 gallons of solution per acre. The compound was applied at the rate of 4 pounds/acre (4.48 kg/ha). The spray solution was made up similarly to that described for the pre-emergence evaluation.

The flats were returned to the greenhouse after spraying and watered daily without wetting the foliage. Three weeks after treatment the degree of weed control was estimated and recorded as percentage control compared to the growth of the same species in an untreated check flat of the same age. The percent control ratings were assigned on the same basis as for the pre-emergence evaluation.

The following Table 2 contains the results of these tests, in terms of average control of the three grasses, three broadleaf weeds, and yellow nutsedge, respectively, in both pre- and post-emergence evaluations.

TABLE 2

| Rating at 4 lb/A | | |
|---|---|---|
| green foxtail | *Setaria viridis* | SETVI |
| watergrass | *Echinochloa crusgalli* | ECHCG |
| wild oat | *Avena fatua* | AVEFA |
| annual morningglory | *Ipomoea purpurea* | PHBPU |
| velvetleaf | *Abutilon theophrasti* | ABUTH |
| wild mustard | *Brassica kaber* | SINAR |
| yellow nutsedge | *Cyperus esculentus* | CYPES |
| AVG | Average grasses | |
| AVB | Average broadleaf | |

Compound

TABLE 2-continued

| No. | METHOD | SETVI | AVEFA | ECHCG | SINAR | ABUTH | PHBPU | CYPES | AVG | AVB |
|---|---|---|---|---|---|---|---|---|---|---|
| 1 | PES | 0 | 0 | 10 | 80 | 90 | 100 | 0 | 3 | 90 |
|   | POS | 0 | 0 | 0 | 0 | 0 | 0 | 0 | 0 | 0 |
| 2 | PES | 0 | 0 | 0 | 0 | 0 | 0 | 0 | 0 | 0 |
|   | POS | 0 | 0 | 0 | 0 | 0 | 0 | 0 | 0 | 0 |
| 3 | PES | 0 | 0 | 0 | 90 | 80 | 10 | 0 | 0 | 60 |
|   | POS | 0 | 0 | 0 | 0 | 0 | 0 | 0 | 0 | 0 |
| 4 | PES | 40 | 10 | 60 | 0 | 0 | 0 | 0 | 37 | 0 |
|   | POS | 0 | 0 | 0 | 0 | 0 | 0 | 0 | 0 | 0 |
| 5 | PES | 0 | 0 | 0 | 0 | 0 | 0 | 0 | 0 | 0 |
|   | POS | 0 | 0 | 0 | 10 | 10 | 5 | 0 | 0 | 8 |
| 6 | PES | 0 | 0 | 0 | 0 | 0 | 0 | 0 | 0 | 0 |
|   | POS | 0 | 0 | 0 | 0 | 0 | 0 | 0 | 0 | 0 |
| 7 | PES | 0 | 0 | 0 | 100 | 90 | 20 | 0 | 0 | 70 |
|   | POS | 0 | 0 | 0 | 0 | 0 | 0 | 0 | 0 | 0 |
| 8 | PES | 0 | 0 | 0 | 90 | 80 | 0 | 0 | 0 | 57 |
|   | POS | 60 | 20 | 10 | 90 | 0 | 0 | 0 | 30 | 30 |
| 9 | PES | 0 | 0 | 0 | 0 | 0 | 0 | 0 | 0 | 0 |
|   | POS | 100 | 0 | 0 | 80 | 60 | 5 | 0 | 33 | 48 |
| 10 | PES | 0 | 0 | 0 | 95 | 95 | 25 | 0 | 0 | 72 |
|   | POS | 0 | 0 | 0 | 0 | 0 | 0 | 0 | 0 | 0 |
| 11 | PES | 0 | 0 | 0 | 0 | 0 | 0 | 0 | 0 | 0 |
|   | POS | 0 | 0 | 0 | 0 | 0 | 0 | 0 | 0 | 0 |
| 12 | PES | 100 | 0 | 0 | 0 | 0 | 0 | 0 | 33 | 0 |
|   | POS | 0 | 0 | 0 | 0 | 0 | 0 | 0 | 0 | 0 |
| 13 | PES | 80 | 0 | 0 | 0 | 0 | 0 | 0 | 27 | 0 |
|   | POS | 0 | 0 | 0 | 10 | 10 | 10 | 0 | 0 | 10 |
| 14 | PES | 90 | 0 | 0 | 0 | 0 | 0 | 0 | 30 | 0 |
|   | POS | 0 | 0 | 0 | 0 | 0 | 0 | 0 | 0 | 0 |
| 15 | PES | 0 | 0 | 0 | 10 | 5 | 0 | 0 | 0 | 5 |
|   | POS | 0 | 0 | 0 | 20 | 10 | 0 | 0 | 0 | 10 |
| 16 | PES | 0 | 0 | 10 | 100 | 10 | 0 | 0 | 7 | 37 |
|   | POS | 0 | 0 | 0 | 50 | 10 | 0 | 0 | 0 | 20 |
| 17 | PES | 50 | 0 | 0 | 100 | 100 | 80 | 0 | 17 | 93 |
|   | POS | 0 | 0 | 0 | 0 | 0 | 0 | 0 | 0 | 0 |
| 18 | PES | 0 | 0 | 0 | 0 | 0 | 0 | 0 | 0 | 0 |
|   | POS | 0 | 0 | 0 | 0 | 0 | 0 | 0 | 0 | 0 |
| 19 | PES | 0 | 0 | 0 | 0 | 0 | 0 | 0 | 0 | 0 |
|   | POS | 0 | 0 | 0 | 0 | 0 | 0 | 0 | 0 | 0 |
| 20 | PES | 0 | 0 | 0 | 50 | 30 | 10 | 0 | 0 | 30 |
|   | POS | 0 | 0 | 0 | 0 | 0 | 0 | 0 | 0 | 0 |
| 21 | PES | 100 | 0 | 0 | 100 | 100 | 100 | 0 | 33 | 100 |
|   | POS | 0 | 0 | 0 | 100 | 0 | 25 | 0 | 0 | 42 |
| 22 | PES | 100 | 90 | 100 | 100 | 100 | 100 | 0 | 97 | 100 |
|   | POS | 0 | 0 | 0 | 100 | 100 | 100 | 0 | 0 | 100 |
| 23 | PES | 10 | 20 | 20 | 100 | 90 | 0 | 0 | 17 | 63 |
|   | POS | 0 | 0 | 0 | 10 | 10 | 10 | 0 | 0 | 10 |
| 24 | PES | 20 | 20 | 20 | 100 | 80 | 10 | 0 | 20 | 63 |
|   | POS | 0 | 0 | 0 | 100 | 100 | 85 | 0 | 0 | 95 |
| 25 | PES | 0 | 0 | 0 | 0 | 0 | 0 | 0 | 0 | 0 |
|   | POS | 0 | 0 | 0 | 0 | 0 | 0 | 0 | 0 | 3 |
| 26 | PES | 100 | 100 | 100 | 100 | 100 | 75 | 0 | 100 | 92 |
|   | POS | 20 | 20 | 20 | 100 | 100 | 60 | 0 | 20 | 87 |
| 27 | PES | 90 | 100 | 100 | 100 | 100 | 75 | 0 | 97 | 92 |
|   | POS | 0 | 0 | 0 | 100 | 100 | 10 | 0 | 0 | 70 |
| 28 | PES | 10 | 10 | 10 | 0 | 0 | 0 | 0 | 10 | 0 |
|   | POS | 0 | 0 | 0 | 0 | 0 | 0 | 0 | 0 | 0 |
| 29 | PES | 0 | 0 | 0 | 0 | 0 | 0 | 0 | 0 | 0 |
|   | POS | 0 | 0 | 0 | 10 | 0 | 0 | 0 | 0 | 3 |
| 30 | PES | 100 | 0 | 0 | 0 | 0 | 0 | 0 | 33 | 0 |
|   | POS | 100 | 0 | 0 | 0 | 0 | 0 | 0 | 33 | 0 |
| 31 | PES | 50 | 0 | 0 | 0 | 0 | 0 | 0 | 17 | 0 |
|   | POS | 0 | 0 | 0 | 0 | 0 | 0 | 0 | 0 | 0 |
| 32 | PES | 0 | 0 | 0 | 0 | 0 | 0 | 0 | 0 | 0 |
|   | POS | 0 | 0 | 0 | 0 | 0 | 0 | 0 | 0 | 0 |
| 33 | PES | 0 | 0 | 0 | 0 | 0 | 0 | 0 | 0 | 0 |
|   | POS | 0 | 0 | 0 | 0 | 0 | 0 | 0 | 0 | 0 |
| 34 | PES | 100 | 10 | 60 | 100 | 10 | 10 | 0 | 57 | 40 |
|   | POS | 0 | 0 | 0 | 90 | 20 | 0 | 0 | 0 | 37 |
| 35 | PES | 20 | 0 | 0 | 0 | 0 | 0 | 0 | 7 | 0 |
|   | POS | 0 | 0 | 0 | 0 | 0 | 0 | 0 | 0 | 0 |
| 36 | PES | 100 | 40 | 20 | 95 | 100 | 70 | 0 | 53 | 88 |
|   | POS | 60 | 60 | 40 | 100 | 100 | 100 | 0 | 53 | 100 |
| 37 | PES | 100 | 100 | 100 | 100 | 100 | 100 | 0 | 100 | 100 |
|   | POS | 100 | 90 | 80 | 100 | 100 | 100 | 0 | 90 | 100 |
| 38 | PES | 0 | 0 | 0 | 0 | 50 | 20 | 0 | 0 | 23 |
|   | POS | 0 | 0 | 0 | 0 | 0 | 0 | 0 | 0 | 0 |
| 39 | PES | 0 | 0 | 0 | 0 | 0 | 0 | 0 | 0 | 0 |
|   | POS | 0 | 0 | 0 | 0 | 0 | 0 | 0 | 0 | |
| 40 | PES | 0 | 0 | 0 | 0 | 0 | 0 | 0 | 0 | 0 |
|   | POS | 0 | 0 | 0 | 0 | 0 | 0 | 0 | 0 | 0 |
| 41 | PES | 100 | 60 | 10 | 0 | 0 | 0 | 0 | 57 | 0 |

TABLE 2-continued

|    |     |     |    |    |     |     |    |    |    |     |
|----|-----|-----|----|----|-----|-----|----|----|----|-----|
|    | POS | 0   | 0  | 0  | 0   | 0   | 0  | 0  | 0  | 0   |
| 42 | PES | 95  | 80 | 70 | 100 | 100 | 80 | 0  | 82 | 93  |
|    | POS | 0   | 0  | 0  | 100 | 100 | 25 | 0  | 0  | 75  |
| 43 | PES | 0   | 0  | 0  | 0   | 0   | 0  | 0  | 0  | 0   |
|    | POS | 0   | 0  | 0  | 0   | 0   | 0  | 0  | 0  | 0   |
| 44 | PES | 100 | 20 | 0  | 100 | 20  | 10 | 0  | 40 | 43  |
|    | POS | 0   | 0  | 0  | 0   | 0   | 0  | 0  | 0  | 0   |
| 45 | PES | 0   | 0  | 20 | 100 | 100 | 100 | 0 | 7  | 100 |
|    | POS | 0   | 0  | 0  | 0   | 0   | 0  | 0  | 0  | 0   |
| 46 | PES | 100 | 80 | 80 | 100 | 100 | 80 | 0  | 87 | 93  |
|    | POS | 0   | 0  | 0  | 0   | 0   | 0  | 0  | 0  | 0   |
| 47 | PES | 0   | 0  | 0  | 0   | 0   | 0  | 0  | 0  | 0   |
|    | POS | 100 | 0  | 0  | 100 | 100 | 0  | 0  | 33 | 67  |
| 48 | PES | 100 | 20 | 90 | 80  | 100 | 50 | 40 | 70 | 77  |
|    | POS | 0   | 0  | 0  | 0   | 0   | 0  | 0  | 0  | 0   |
| 49 | PES | 100 | 20 | 90 | 100 | 100 | 50 | 40 | 70 | 83  |
|    | POS | 80  | 0  | 0  | 80  | 100 | 0  | 0  | 27 | 60  |
| 50 | PES | 85  | 0  | 10 | 0   | 0   | 0  | 0  | 32 | 10  |
|    | POS | 0   | 0  | 0  | 0   | 0   | 0  | 0  | 0  | 0   |

Formulations

In practice, a pure compound can be used as a herbicide. However, in general, the compounds are first formulated with one or more inert carriers or diluents suitable for herbicidal use, before being applied.

The compositions or formulations, including a compound as described herein, may exist in any one of a number of solid or liquid forms. Examples of solid forms are dusts, granules, microcapsules, tablets, powders and the like. Examples of liquid forms are emulsifiable concentrates, flowables, liquid concentrates and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Microcapsules consist of fully enclosed droplets or granules containing the active materials in which the enclosing material is an inert porous membrane, arranged to allow escape of the enclosed materials to the surrounding medium at controlled rates over a specified period of time. Encapsulated droplets are typically about 1 to 50 microns in diameter. The enclosed liquid typically constitutes about 50 to 95% of the weight of the entire capsule, and may contain an amount of solvent in addition to the active materials. Encapsulated granules are characterized, by porous membranes sealing the openings of the granule carrier pores, trapping the liquid containing the active components inside for controlled release. A typical granule size ranges from 1 millimeter to 1 centimeter in diameter. In agricultural usage, the granule size is generally about 1 to 2 millimeters in diameter. Granules formed by extrusion, agglomeration or prilling are useful in the present invention, as well as the materials in their naturally occurring form. Examples of such carriers are vermiculite, sintered clay granules, kaolin, attapulgite clay, sawdust and granular carbon. Useful encapsulating materials include natural and synthetic rubbers, cellulosic materials, styrene-butadiene copolymers, polyacrylonitriles, polyacrylates, polyesters, polyamides, polyureas, polyurethanes and starch xanthates.

Wettable powders, flowables, and pastes are obtained by mixing and milling an active compound with one or more dispersing/wetting agents and/or carriers or diluents. Common dispersing/wetting agents are, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes or higher boiling aromatic hydrocarbons. To obtain stable suspensions or emulsions in application water, wetting agents are generally also added.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders, flowables and pastes—20 to 90% active compound; oil suspensions, emulsions, solutions and emulsifiable concentrates—1 to 90% active compound; aqueous suspensions—10 to 50% active compound; dusts and powders—1 to 25% active compound; granules and pellets—0.5 to 20% active compound.

The rate of application of the active compound to a locus to be controlled will depend on the nature of the seeds and plants to be controlled and will vary from about 0.05 to about 50 pounds per acre (about 0.06 to about 56 kg/ha).

In addition to the active compound and the various agents utilized in preparing compositions and formulations mentioned above, such compositions may also contain one or more other active compounds of the type mentioned herein as well as other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or of the compounds described herein as well as, optionally, other pesticides and also fertilizers, all intended and formulated for use at the same locus.

Examples of other herbicides, defoliants, dessicants and plant growth inhibitors with which the compounds of this invention can be combined are:

chlorophenoxy herbicides such as 2,4-D, 2,4,5-T, MCPA, MCPB, 2,4-DB, 2,4-DEB, 4-CPA, 2,4,5-TB and silvex;

carbamate herbicides such as propham, chlorpropham, swep and barban;

thiocarbamate and dithiocarbamate herbicides such as CDEC, metham-sodium, EPTC, diallate, PEBC, perbulate and vernolate;

substituted urea herbicides such as norea, sifuron, dichloral ureal, chloroxuron, cycluron, fenuron, monuron, monuron TCA, diuron, linuron, monolinuron neburon, buturon and trimeturon;

symmetrical triazine herbicides such as simazine, chlorazine, desmetryne, norazine, ipazine, prometryn, atrazine, trietazine, simetone, prometone, propazine and ametryne;

chloroacetamide herbicides such as 4-(chloroacetyl)-morpholine and 1-(chloroacetyl)piperidine;

chlorinated aliphatic acid herbicides such as TCA, dalapon, 2,3-dichloropropionic acid and 2,2,3-TPA;

chlorinated benzoic acid and phenylacetic acid herbicides such as 2,3,6-TBA, 2,3,5,6-TBA, dicamba, tricamba, chloramben, fenac, PBA, 2-methoxy-3,6-dichlorophenylacetic acid, 3-methoxy-2,6-dichlorophenylacetic acid, 2-methoxy-3,5,6-trichlorophenylacetic acid and 2,4-dichloro-3-nitrobenzoic acid;

and such compounds as aminotriazole, maleic hydrazide, phenylmercury acetate, endothal, biuret, technical chlordane, diquat, erbon, DNC, DNBP, dichlobenil, DPA, diphenamide, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, alachlor, nitralin, sodium tetraborate, calcium cyanamid, sindone, sindone B, propanil and S,S,S-tributylphoshorotrithioate.

Compositions containing one or more of the active compounds described, in a herbicidally effective amount, may be applied to the plant or locus to be controlled in any conventional manner. Thus, powders and various liquid or microencapsulated compositions containing the active compound can be applied by the use of power dusters, boom and hand sprayers and spray dusters, or applied from airplanes as mists or sprays.

When applied in the latter method they may be effective in very low dosages. To modify or control growth of germinating seeds or emerging seedlings, dusts and liquid compositions may be applied to the soil with conventional methods and may be distributed in the soil to a depth of one-half inch below the soil surface. In some instances, the compositions need not be admixed with the soil particles but can be applied merely by sprinkling on the surface of the soil. Incorporation of dust, granular, microencapsulated or liquid soil surface applied formulations can be distributed below the soil surface by conventional means such as disking, dragging or other mixing operations.

Compositions including active compounds may also be applied by addition to irrigation waters supplied to the field to be treated. This method of application permits penetration of the compounds into the soil as the water is absorbed therein.

EXAMPLES OF TYPICAL COMPOSITIONS

Dusts: The following substances are used to formulate (a) a 5% and (b) a 2% dust:

(a)
5 parts of active substance
95 parts of talc;
(b)
2 parts of active substance
1 part of highly dispersed silicic acid
97 parts of talc.

The active substances are mixed with the carriers and ground and in this form can be processed to dusts for application.

Granulate: The following substances are used to formulate a 5% granulate:

5 parts of active substance
0.25 part of epichlorohydrin
0.25 part of cetyl polyglycol ether
3.25 parts of polyethylene glycol
91 parts of kaolin (particle size 0.3–0.8 mm)

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo.

Wettable Powders: The following constituents are used to formulate (a) a 70%; (b) a 40%; (c) and (d) a 25%; and (e) a 10% wettable powder:

(a)
70 parts of active substance
5 parts of sodium dibutylnaphthylsulfonate
3 parts of naphthalenesulfonic acid/phenolsulfonic acid/formaldehyde condensate (3:2:1)
10 parts of kaolin
12 parts of Champagne chalk
(b)
40 parts of active substance
5 parts of sodium lignin sulfonate
1 part of sodium dibutylnaphthalenesulfonic acid
54 parts of silicic acid
(c)
25 parts of active substance
4.5 parts of calcium lignin sulfonate
1.9 parts of Champagne chalk/hydroxyethyl cellulose mixture (1:1)
1.5 parts of sodium dibutylnaphthalenesulfonate
19.5 parts of silicic acid
19.5 parts of Champagne chalk
28.1 parts of kaolin (d)
25 parts of active substance
2.5 parts of isooctylphenoxy-polyethylene-ethanol
1.7 parts of Champagne chalk/hydroxyethyl cellulose mixture (1:1)
8.3 parts of sodium aluminum silicate
16.5 parts of kieselguhr
46 parts of kaolin (e)
10 parts of active substance
3 parts of a mixture of the sodium salts of saturated fatty alcohol sulfates
5 parts of naphthalenesulfonic acid/formaldehyde condensate
82 parts of kaolin The active substances are intimately mixed in suitable mixers with the additives and ground in appropriate mills and rollers. Wettable powders of excellent wettability and suspension power are obtained. These wettable powders can be diluted with water to give suspensions of the desired concentration and can be used in particular for treating parts of plants.

Emulsifiable Concentrate: The following substances are used to formulate a 25% emulsifiable concentrate:
25 parts of active substance
2.5 parts of epoxidized vegetable oil
10 parts of an alkylarylsulfonate/fatty alcohol polyglycol ether mixture
5 parts of dimethylformamide
57.5 parts of xylene By diluting such a concentrate with water, it is possible to prepare emulsions of the desired concentrations, which are especially suitable for leaf application.

Although the present invention has been described in some detail by way of examples for purposes of clarity and understanding, it will be apparent that other arrangements and equivalents are possible and may be employed without departing from the spirit and scope of the invention. Therefore, the description and illustrations should not be construed as limiting the scope of the invention, which is delineated by the appended claims.

What is claimed is:

1. A compound having the formula

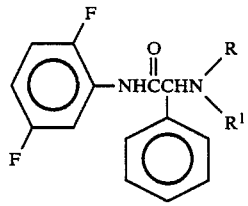

wherein
R is $C_1$-$C_3$ alkyl or phenyl;
$R^1$ is selected from the group consisting of amino, substituted carbonyl wherein said substituent is $C_1$-$C_4$ alkylthio, carboxy, phenylthio, or $C_1$-$C_4$ alkylamino; and $C_2$-$C_4$ alkylthio thiocarbonyl.

2. A compound according to claim 1 in which $R^1$ is selected from the group consisting of substituted carbonyl wherein said substituent is carboxy, or $C_1$-$C_4$ alkylamino; and $C_2$-$C_4$ alkylthio thiocarbonyl.

3. A compound according to claim 1 in which R is $C_1$-$C_3$ alkyl; $R^1$ is selected from the group consisting of amino and substituted carbonyl wherein the substituent is selected from alkylthio or phenylthio.

4. A compound according to claim 3 in which R is $C_1$-$C_2$ alkyl; $R^1$ is selected from the group consisting of amino and substituted carbonyl wherein said substituent is $C_1$-$C_2$ alkylthio.

5. A compound according to claim 4 in which R is methyl; $R^1$ is selected from the group consisting of amino and substituted carbonyl wherein said substituent is methylthio or ethylthio.

6. A compound according to claim 1 in which R is methyl, and $R^1$ is amino.

7. A compound according to claim 1 in which R is methyl, and $R^1$ is ethylthio carbonyl.

8. A compound according to claim 1 in which R is methyl, and $R^1$ is methylthio carbonyl.

9. A herbicidal composition comprising:
(a) a herbicidally effective amount of a compound having the formula

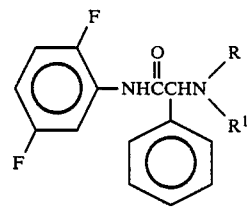

R is $C_1$-$C_3$ alkyl or phenyl;
$R^1$ is selected from the group consisting of amino, substituted carbonyl wherein said substituent is $C_1$-$C_4$ alkylthio, carboxy, phenylthio, or $C_1$-$C_4$ alkylamino; and $C_2$-$C_4$ alkylthio thiocarbonyl; and
(b) a herbicidally suitable inert solvent or carrier.

10. A herbicidal composition according to claim 9 in which $R_1$ is selected from the group consisting of substituted carbonyl wherein said substituent is carboxy, and $C_2$-$C_4$ alkylthio thiocarbonyl.

11. A herbicidal composition according to claim 9 in which R is $C_1$-$C_3$ alkyl, $R_1$ is selected from the group consisting of amino and substituted carbonyl wherein the substituent is selected from alkylthio and phenylthio.

12. A herbicidal composition according to claim 9 in which R is $C_1$-$C_2$ alkyl; $R^1$ is selected from the group consisting of amino and substituted carbonyl wherein said substituent is $C_1$-$C_2$ alkylthio.

13. A herbicidal composition according to claim 12 in which R is methyl; $R^1$ is selected from the group consisting of amino and substituted carbonyl wherein said substituent is methylthio or ethylthio.

14. A herbicidal composition according to claim 9 in which R is methyl, and $R^1$ is amino.

15. A herbicidal composition according to claim 9 in which R is methyl, and $R^1$ is ethylthio carbonyl.

16. A herbicidal composition according to claim 9 in which R is methyl, and $R^1$ is methylthio carbonyl.

17. A method of controlling undesirable vegetation comprising applying to said vegetation or to the locus thereof a herbicidally effective amount of a compound having the formula

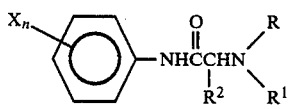

wherein

R is $C_1$–$C_3$ alkyl or phenyl;

$R^1$ is selected from the group consisting of amino, $C_1$–$C_4$ alkyl, allyl, substituted carbonyl wherein said substituent is $C_1$–$C_4$ haloalkyl, $C_2$–$C_4$ alkoxycarbonyl, $C_1$–$C_4$ alkylthio, carboxy, $C_1$–$C_5$ alkoxy, $C_1$–$C_4$ alkyl, vinyl, haloanilino, phenylthio, $C_1$–$C_4$ alkylamino, benzylamino, $C_3$–$C_6$ alkoxycarbonylalkyl or substituted carbamyl wherein the substituent is $C_1$–$C_2$ alkyl halocarbanilide; $C_2$–$C_4$ alkylthio thiocarbonyl; mono-haloanilino carbonylmethylene, $C_1$–$C_3$ alkoxy carbonylmethylene, and carboxymethylene;

$R^2$ is phenyl;

X is halo or $C_1$–$C_2$ haloalkyl; and n is an integer selected from 1–3 inclusive.

18. A herbicidal method according to claim 17 in which $R^1$ is selected from the group consisting of $C_1$–$C_4$ alkyl, substituted carbonyl wherein said substituent is $C_2$–$C_4$ alkoxycarbonyl, carboxy, $C_1$–$C_4$ alkyl, vinyl, haloanilino, $C_1$–$C_4$ alkylamino, benzylamino, $C_3$–$C_6$ alkoxycarbonylalkyl or substituted carbamyl wherein the substituent is $C_1$–$C_2$ alkyl halocarbanilide; $C_2$–$C_4$ alkylthio thiocarbonyl; mono-haloanilino carbonylmethylene and $C_1$–$C_3$ alkoxy carbonylmethylene.

19. A herbicidal method according to claim 17 in which R is $C_1$–$C_3$ alkyl; $R^1$ is selected from the group consisting of amino, carboxymethylene, allyl, and substituted carbonyl wherein the substituent is selected from alkylthio, alkoxy, trifluoromethyl and phenylthio; $R^2$ is phenyl; X is halo; and n is an integer selected from 1–3, inclusive.

20. A herbicidal method according to claim 19 in which R is $C_1$–$C_2$ alkyl; $R^1$ is selected from the group consisting of amino and substituted carbonyl wherein said substituent is halomethyl, $C_1$–$C_2$ alkylthio or $C_1$–$C_2$ alkoxy; and X is dihalo.

21. A herbicidal method according to claim 20 in which R is methyl; $R^1$ is selected from the group consisting of amino and substituted carbonyl wherein said substituent is trifluoromethyl, methylthio, ethylthio, methoxy or ethoxy; and X is difluoro.

22. A herbicidal method according to claim 17 in which X is 2,5-difluoro, R is methyl, $R^1$ is amino and $R^2$ is phenyl.

23. A herbicidal method according to claim 17 in which X is 2,5-difluoro, R is methyl, $R^1$ is ethylthio carbonyl and $R^2$ is phenyl.

24. A herbicidal method according to claim 17 in which X is 2,5-difluoro, R is methyl, $R^1$ is ethoxy carbonyl and $R^2$ is phenyl.

25. A herbicidal method according to claim 17 in which X is 2,5-difluoro, R is methyl, $R^1$ is methylthio carbonyl and $R^2$ is phenyl.

26. A herbicidal method according to claim 17 in which X is 2,5-difluoro, R is methyl, $R^1$ is methoxy carbonyl and $R^2$ is phenyl.

* * * * *